United States Patent
Ivanov et al.

(10) Patent No.: US 8,762,400 B2
(45) Date of Patent: Jun. 24, 2014

(54) METHOD OF COLLECTING DATA

(75) Inventors: Eugene Ivanov, Eindhoven (NL); Alexander Wilhelmus Heerink, Wierden (NL)

(73) Assignee: Koninklijke Philips N.V., Eindhoven (NL)

( * ) Notice: Subject to any disclaimer, the term of this patent is extended or adjusted under 35 U.S.C. 154(b) by 771 days.

(21) Appl. No.: 12/305,414

(22) PCT Filed: Jun. 12, 2007

(86) PCT No.: PCT/IB2007/052221
§ 371 (c)(1),
(2), (4) Date: Dec. 18, 2008

(87) PCT Pub. No.: WO2007/148259
PCT Pub. Date: Dec. 27, 2007

(65) Prior Publication Data
US 2009/0228448 A1    Sep. 10, 2009

(30) Foreign Application Priority Data
Jun. 22, 2006 (EP) .................................. 06115857

(51) Int. Cl.
*G06F 7/00* (2006.01)
*G06F 17/30* (2006.01)

(52) U.S. Cl.
USPC ........................................................ 707/758

(58) Field of Classification Search
USPC ........................................................ 707/758
See application file for complete search history.

(56) References Cited

U.S. PATENT DOCUMENTS

| | | |
|---|---|---|
| 6,259,944 B1 | 7/2001 | Margulis et al. |
| 6,454,708 B1 * | 9/2002 | Ferguson et al. ............. 600/300 |
| 6,897,788 B2 | 5/2005 | Khair et al. |
| 2002/0052851 A1 | 5/2002 | Berman |
| 2005/0203973 A1 | 9/2005 | Yagawa |
| 2005/0206518 A1 | 9/2005 | Welch et al. |
| 2006/0004264 A1 * | 1/2006 | Rudowski et al. ............. 600/300 |
| 2006/0004818 A1 | 1/2006 | Claudatos et al. |

FOREIGN PATENT DOCUMENTS

GB    2415786 A    1/2006

OTHER PUBLICATIONS

Yu Ma et al: "A composable data management architecture for scientific applications" Challenges of Large Applications in Distributed Environments, 2005. Clade 2005. Proceedings Research Triangle Park, NC, USA Jul. 24, 2005, Piscataway, NJ, USA,IEEE, Jul. 24, 2005, pp. 35-44, XP010843359 ISBN: 0-7803-9043-1.

Reilly D N: "Boosting Raid Performance With Solid State Disks" Computer Technology Review, Westworld Production, Beverly Hill, CA, US, vol. 15, No. 10, Oct. 1, 1995, pp. 50-52, XP000538282 ISSN: 0278-9647.

Levy E et al: "Distributed file systems: concepts and examples" Dec. 1990, ACM Computing Surveys, ACM, New York, NY, US, US, pp. 321-374, XP002392825 ISSN: 0360-0300 abstract.

* cited by examiner

*Primary Examiner* — Alexey Shmatov

(57) ABSTRACT

Data storage method for storing a subblock of a block of data. The block of data is distributed, in a number of subblocks of data, over a set of devices. The set of devices comprises at least two devices, and the method comprises the steps of: collecting a subblock of data using the device, storing the subblock of data on the device; and storing metadata identifying the data comprised in the subblock of data.

13 Claims, 2 Drawing Sheets

METHOD OF COLLECTING DATA

FIELD OF THE INVENTION

The present invention relates to a method of collecting data and in particular to a method of collecting a part of a block of data, the block of data being distributed, in a number of subblocks of data, over a set of devices.

BACKGROUND OF THE INVENTION

For monitoring a patient, for example a heartbeat rhythm of the patient, it is known to have the patient wear a telemonitoring device. A telemonitoring device, being a part of a telemonitoring system, is a battery-operated wearable device continuously collecting data from the patient. The patient data are locally stored on the telemonitoring device.

A known telemonitoring system comprises a number of telemonitoring devices such that a battery of a first telemonitoring device may be (re-)charged, while a second telemonitoring device is worn and collects patient data. When the battery of the second telemonitoring device is exhausted, for example, a switch to the first telemonitoring device is made. Consequently, in the end, a part of the collected patient data is stored on the first telemonitoring device, while another part of the collected patient data is stored on the second telemonitoring device.

Apart from collecting patient data, the telemonitoring device may detect abnormalities in e.g. the heart rhythm of the patient and, in response thereto, send an alarm (alert) signal to a monitoring center through a suitable communication connection, e.g. using a mobile phone system. Such an alarm signal may comprise the patient data collected just prior to sending the alarm signal, i.e including the data relating to the detected abnormality. In the monitoring center, a person skilled in analyzing and evaluating the patient data may review the patient data comprised in the alarm signal.

In certain instances, the evaluating person may request additional data, for example data relating to a longer time period prior to the detected abnormality. The request may be sent to the telemonitoring device worn by the patient. However, as described above, the requested patient data may be distributed over the number of telemonitoring devices. As it may be unknown to the evaluating person, and to the patient, on which telemonitoring device the requested data are stored, it is known to send each telemonitoring device to the evaluating person. In order to enable telemonitoring while the data are being collected, analyzed and evaluated, the patient may be provided with replacement telemonitoring devices.

Considering that the block of patient data is distributed, in an unknown number of subblocks of patient data, over an unknown number of telemonitoring devices, a problem of the method and system is that a predetermined part of the patient data has to be retrieved from the number of telemonitoring devices.

OBJECT OF THE INVENTION

It is desirable to have a method and a telemonitoring system wherein a predetermined part of a block of patient data is easily and quickly retrievable from the patient data that are distributed, in a number of subblocks of data, over a number of telemonitoring devices.

SUMMARY OF THE INVENTION

In an aspect, the present invention provides a method of storing data according to claim 1 and a data collection method according to claim 5.

In the data storage method according to the invention, a subblock of data is collected and stored on the device. Further, metadata identifying the data comprised in the subblock of data is stored.

Thus, after storage according to the present invention, a predetermined part of the block of data distributed over a number of devices may be easily retrieved by querying the metadata of each device, thereby identifying the corresponding subblocks of data. From the metadata it is derivable which devices store subblocks of data, which subblocks together comprise the predetermined part of the block of data.

The metadata may comprise a device identification code, a data collection time period, a patient or user identification code and/or any other relevant information.

In an embodiment of the storage method, the metadata is stored on the device. Therefore, upon a request for data, each device may be queried by requesting the stored metadata. If a device stores a subblock of data comprising requested data as determined from the metadata, the device is requested to provide said subblock of data. Thus, by querying each device and gathering all subblocks of data comprising requested data, the predetermined part of the block of data is gathered without the necessity to query or collect all data from each device.

In a practical embodiment of the telemonitoring system, only an active telemonitoring device is available for communication. The active telemonitoring device is the device collecting patient data. At the same time, the other telemonitoring devices may be (re)charged or switched off, or the like. In order to prevent that all telemonitoring devices need to have been active for gathering all metadata, in an embodiment of the storage method, the metadata is stored in an external memory. Such an external memory may be comprised in a communication device, such as a (mobile) phone or the like, or the external memory may be located at the monitoring center. In such an embodiment, the external device and the telemonitoring device may synchronize with each other prior to the exchange of metadata in order to prevent errors due to different settings, like non-synchronized clocks.

The collected patient data is stored on the active telemonitoring device. For retrieving the patient data, the patient data may be transferred to another device or the device may be sent to the monitoring center. In an embodiment, the patient data is stored on a removable memory device. Thus, the memory device may be removed from the telemonitoring device and possibly replaced by another memory device. The removed memory device storing the patient data may be sent to the monitoring center or may be read by a device suitable for reading the memory and communicating the read data to the telemonitoring center through a suitable communication connection. Such a suitable connection may be realized over different networks, e.g., mobile wireless communication networks or data networks such as the Internet.

In an embodiment of the data collection method, the method comprises retrieving metadata from each device of the set of devices. In another embodiment, the method comprises retrieving the metadata from an external memory, for instance a memory of a communication device, such as a (mobile) phone or the like, or the external memory may be located at the monitoring center. The embodiment of the data collection method depends on the embodiment of the corresponding storage method.

In a further aspect of the present invention, a telemonitoring system is provided, the system comprising a telemonitoring device comprising a memory for storing a subblock of data and being configured for storing metadata identifying data comprised in the subblock of data. The telemonitoring device may comprise an identification object, such as a visible label, a visible text, an RF-ID transponder, or the like. In an embodiment, the memory is a removable memory.

BRIEF DESCRIPTION OF THE DRAWINGS

Hereinafter, the present invention is elucidated in more detail with reference to the appended drawings illustrating non-limiting embodiments, wherein.

DETAILED DESCRIPTION OF EXAMPLES

Figure 1:
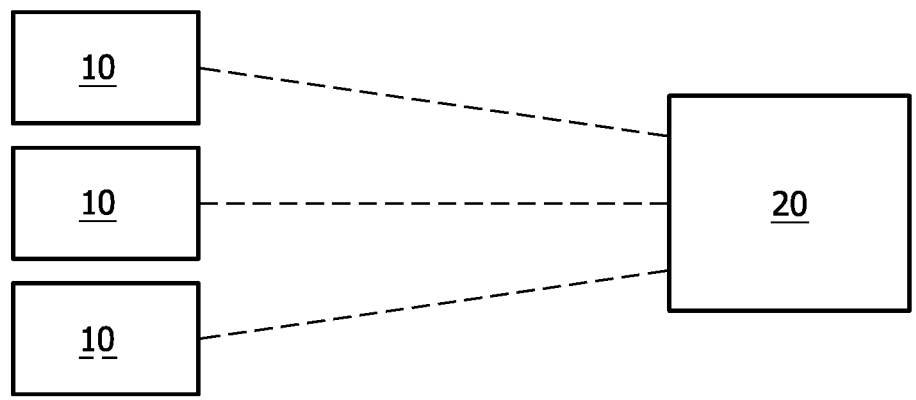
FIG. 1 illustrates a telemonitoring system.

In the drawings, like reference numerals refer to like components. FIG. 1 shows schematically a telemonitoring system. The telemonitoring system comprises at least one telemonitoring device 10 and a monitoring center 20. The telemonitoring system is configured for monitoring a patient, such as a heart patient, without the patient being required to be at a specific location, such as in hospital. Hereinafter, the telemonitoring system is described and illustrated in relation to a patient whose heart is monitored. The present invention, however, is not limited to such a heart patient monitoring system, but is also applicable to any other monitoring system. Moreover, the present invention may be applicable in any system in which an amount of data is distributed over and stored in a memory of a number of separate devices.

Referring to FIG. 1, a telemonitoring device 10 is worn by a patient. The telemonitoring device 10 may, for example, comprise a sensor for registering a heartbeat of the patient. Thus, patient data is collected. The telemonitoring may further comprise a storage device for storing the collected patient data. Further, during data collection, the telemonitoring device 10 may analyze the collected data such that an abnormality in the heart rhythm may be detected. Upon detection of an abnormality, the telemonitoring device 10 may then send an alert signal or an alarm signal to the monitoring center 20. Depending on the severeness of the detected abnormality, the alarm signal may be stored at the monitoring center 20 together with heartbeat data relating to the detected abnormality for later review, or in response to the alarm signal, a medically trained person may be sent to the patient for medical assistance.

When reviewing the heartbeat data at a later point in time, for example for diagnosing the patient, more heartbeat data may be required. In such a case a request for more data, in particular predetermined data, like data relating to a longer time period prior to the occurrence of the abnormality or data relating to a same time of other days, is sent to the telemonitoring device 10. In response thereto, the telemonitoring device 10 may send the requested data to the monitoring center 20 or the patient may send the telemonitoring device 10 to the monitoring center 20 by mail.

Figure 2A:
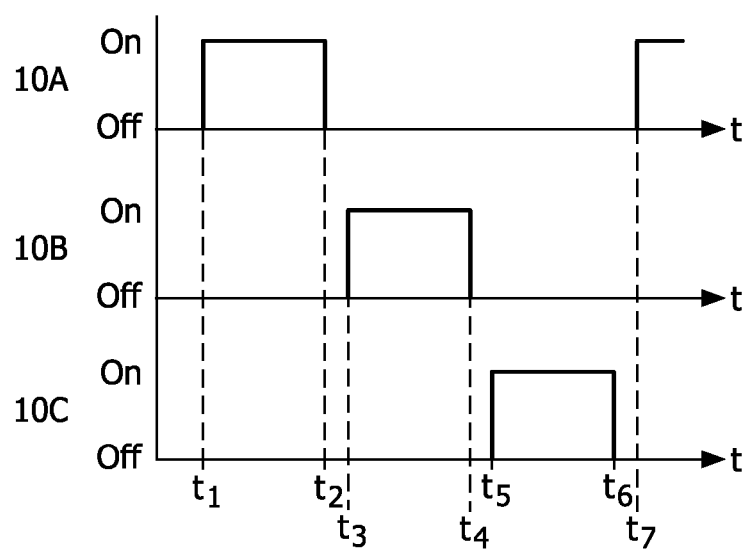
FIG. 2A shows a timing diagram for illustrating an operation of the telemonitoring system of FIG. 1.

In a practical embodiment of the telemonitoring system, however, the collected data is stored in multiple memories of multiple telemonitoring devices 10 as is explained in relation to FIG. 2A. FIG. 2A shows a timing diagram of use of a first telemonitoring device 10A, a second telemonitoring device 10B and a third telemonitoring device 10C. Since the telemonitoring devices 10A-10C are battery-operated for enabling a patient to wear the telemonitoring device 10A-10C, each telemonitoring device 10A-10C needs to be charged when the battery is exhausted. Therefore, when one telemonitoring device 10A-10C is actively collecting data, another telemonitoring device 10A-10C may be (re)charged. The telemonitoring device 10A-10C collecting data may herein be referred to as the active telemonitoring device 10A-10C. A data communication connection may be established only with the active telemonitoring device 10A-10C.

Referring to FIG. 2A, the first telemonitoring device 10A is switched on, i.e. actively collecting heartbeat data, during a first time interval [t1–t2]. The collected heartbeat data is stored in a memory of the telemonitoring device 10A. During the first time interval [t1–t2], the second and third telemonitoring devices 10B and 10C are switched off, i.e. inactive. At time t2, the battery of the first telemonitoring device 10A is exhausted, for example. Therefore, or for any other reason, the first telemonitoring device 10A is switched off. Thereafter, at time t3, the second telemonitoring device 10B is switched on and starts to collect data. The data collected during the second time interval [t3–t4] is stored in a memory of the second telemonitoring device 10B. At time t4, the second telemonitoring device 10B is switched off and at time t5, the third device 10C is switched on. The data collected during the third time interval [t5–t6] is stored in a memory of the third telemonitoring device 10C. At time t7, the first telemonitoring device 10A is used again for collecting data. Thus, a block of data relating to the heartbeat of the patient during the time period [t1–t6] is stored in three subblocks of data, each subblock being stored in a memory of a respective telemonitoring device 10A-10C.

Figure 2B:
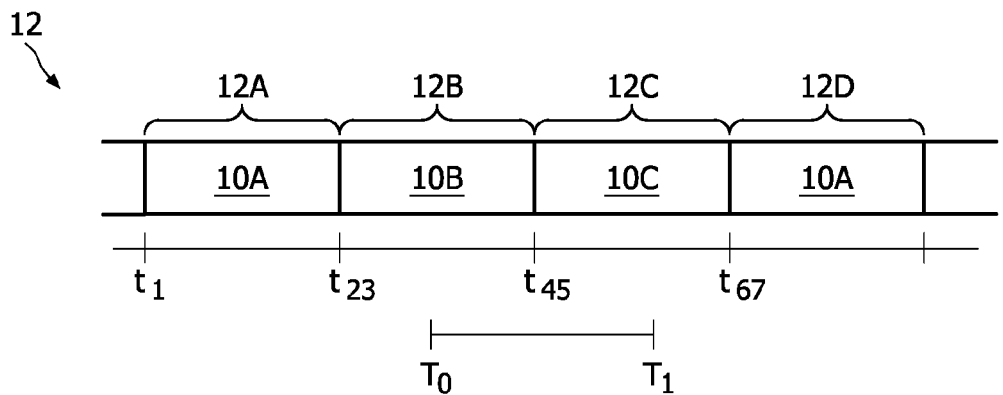
FIG. 2B shows a block of patient data generated by the telemonitoring system of FIG. 1.

In FIG. 2B, a block 12 of data is illustrated. The data block 12 comprises a first subblock 12A, a second subblock 12B, a third subblock 12C and a fourth subblock 12D. Referring to FIGS. 2A and 2B, the first data subblock 12A comprises patient data collected during the first time interval [t1–t2]; the second data subblock 12B comprises data collected during the second time interval [t3–t4]; and the third data subblock 12C comprises data collected during the third time interval [t5–t6]. The fourth data subblock 12D comprises data collected after time t7 and stored in the memory of the first telemonitoring device 10A. Since no data is collected in the time intervals [t2–t3], [t4–t5] and [t6–t7], the data block 12 does not comprise data relating to those time intervals and the boundaries between the data subblocks are indicated to be at a time t23, t45, t67, respectively. It is noted that in an embodiment, the data collection time periods may be consecutive or may overlap.

If, for evaluation, patient data is requested, for example patient data relating to a time period [T0–T1], the relevant data is comprised in the second subblock 12B and the third subblock 12C and is thus distributed over the second telemonitoring device 10B and the third telemonitoring device 10C. However, a data communication connection may be established only with the active telemonitoring device 10A. Since the active telemonitoring device 10A does not store the relevant data, it may be unknown on which telemonitoring devices 10B-10C the relevant data are stored. However, for efficient data recovery, metadata is generated during data collection and storage. The metadata comprises at least an indication of the time interval covered by each subblock 12A-12D of patient data, thus providing information on which subblocks are needed to recover the patient data during a selected time interval. Thus, from the metadata it is determined that the subblocks 12B and 12C are needed for evaluation. Then, the relevant patient data may be retrieved from the telemonitoring devices 10B and 10C.

Figure 3:
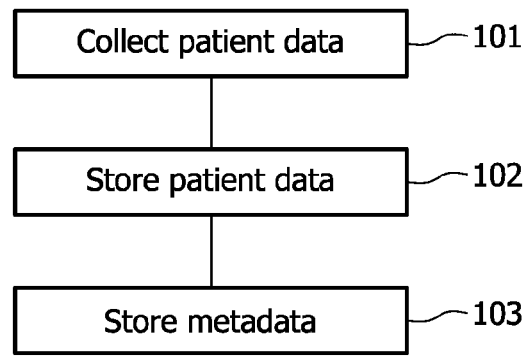
FIG. 3 shows a flow diagram of a data storage method according to the present invention.

FIG. 3 illustrates a data storage method according to the present invention. It is noted that the illustrated method steps 101-103 may be performed sequentially and/or simultaneously. Hence, FIG. 3 is not intended to indicate any kind of temporal relation between the indicated method steps. In a method step 101, patient data is collected by a telemonitoring device. The patient data may be heartbeat data, for example. The patient data is stored according to method step 102. In particular, the patient data is stored in a memory of the telemonitoring device. Further, in a method step 103, metadata about the stored patient data is generated and stored. The metadata may comprise a telemonitoring device identifier, a patient identifier, and a time-interval identifier. The time-interval identifier comprises information on the time interval to which the collected patient data relate. Thus, the metadata may be used for determining which patient data is stored on the telemonitoring device.

The metadata may be stored on the telemonitoring device. Thus, when querying for selected patient data, each telemonitoring device may be requested to supply its metadata in order to determine which telemonitoring device stores relevant data. In an embodiment, one telemonitoring device stores the metadata of each telemonitoring device. In another embodiment, each telemonitoring device stores the metadata of each telemonitoring device.

The metadata may be stored on an external device, such as a phone used for connecting to a monitoring center. For example, common mobile phones comprise a memory. The metadata may be stored in the memory of the mobile phone. Then, when a request from the monitoring center is received by the mobile phone, the metadata stored in the mobile phone may be queried. Then, the mobile phone may indicate which telemonitoring devices store relevant data.

The metadata may be stored on an external device at the monitoring center. Each telemonitoring device supplies the metadata to the external device of the telemonitoring device. When patient data is needed at the telemonitoring center, the request for data sent to the patient may comprise a direct identification of telemonitoring devices storing the relevant data.

The telemonitoring devices may be visually identified by a visual identifier, such as a color of the telemonitoring device or a number or text arranged at an outside of the telemonitoring device. Other kinds of identifiers may be used as well, for example a RF-ID transponder or a bar code.

Figure 4:
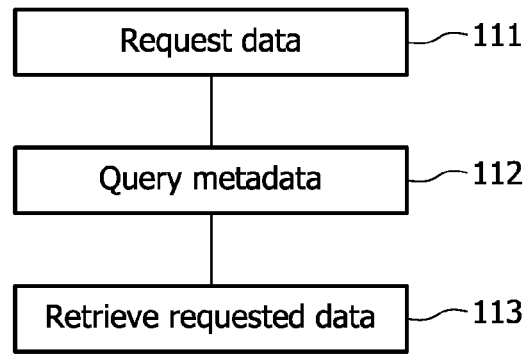
FIG. 4 shows a flow diagram of a data collection method according to the present invention.

FIG. 4 illustrates a data collection method according to the present invention. It is noted that the illustrated method steps 111-113 may be performed sequentially and/or simultaneously. Hence, FIG. 4 is not intended to indicate any kind of temporal relation between the indicated method steps. In a method step 111, it is determined that more patient data is needed, for example for evaluation. The patient data needed may relate to a specific period of time, for example. A request for the patient data is sent to an active telemonitoring device of the patient through a suitable communication connection, such as a telephone connection or any other suitable data network, such as the Internet. In a method step 112, the stored metadata are queried to determine which telemonitoring devices store relevant data relating to the predetermined specific period of time. In a method step 113, the patient data are retrieved from the telemonitoring devices storing the relevant data.

Querying the metadata may be performed at the monitoring center. For example, upon receiving the request for data, the patient sends the telemonitoring devices to the monitoring center by mail. In the monitoring center, a technician may localize and query the metadata, e.g. on each or one telemonitoring device. Using the metadata according to the present invention, only little time is needed to determine which telemonitoring devices store relevant data. It is noted that, in an embodiment, the patient does not send the telemonitoring devices to the monitoring center, but only removable memory devices of the telemonitoring devices storing the patient data.

Querying the metadata may be performed at the patient location. For example, the metadata is stored on an external device, such as a mobile phone, as mentioned above. Then, upon receipt of a request for data relating to a predetermined period of time, the mobile phone, or any other suitable device, may query the metadata stored in the memory of the mobile phone and provide an indication of the telemonitoring devices storing relevant data. Then, using the identifier of the telemonitoring devices, the relevant telemonitoring devices may be gathered and sent to the monitoring center by mail. At the telemonitoring center, the patient data is retrieved from the telemonitoring devices. In another embodiment, the patient data is retrieved at the patient location and sent to the monitoring center by a suitable connection, such as a telephone connection or a data network connection, such as the Internet.

In an embodiment, the request for patient data may carry a delay parameter. For example, if the patient is to send the telemonitoring devices, all of them or only those storing relevant data, replacement telemonitoring devices may be sent to the patient. The delay parameter may be used to provide the patient with information on when the replacement telemonitoring devices are expected to be delivered or the delay parameter may be used to have the request be latent for a period of time until the replacement telemonitoring devices are expected to be delivered.

Although detailed embodiments of the present invention are disclosed herein, it is to be understood that the disclosed embodiments are merely exemplary of the invention, which can be embodied in various forms. Therefore, specific structural and functional details disclosed herein are not to be interpreted in a limiting sense, but merely as a basis for the claims and as a representative basis for teaching a person skilled in the art to variously employ the present invention in virtually any appropriately detailed structure. Further, the mere fact that certain measures are recited in mutually different dependent claims does not indicate that a combination of these measures cannot be used to advantage.

Further, the terms and phrases used herein are not intended to be limiting, but rather to provide an understandable description of the invention. The terms "a" or "an", as used herein, are defined as one or more than one. The term another, as used herein, is defined as at least a second or more. The terms including and/or having, as used herein, are defined as comprising (i.e., open language). The term coupled, as used herein, is defined as connected, although not necessarily directly, and not necessarily by means of wires.

The invention claimed is:

1. Data retrieval method for retrieving multiple blocks of patient data pertaining to the same patient from a memory device that is communicatively coupled to a monitor device, the method comprising:
  identifying a collection time period of interest;
  retrieving metadata identifying a start time of a first collection time period and a stop time of the first collection period, wherein the first collection period is associated with a first block of patient data pertaining to a first patient, wherein the metadata is stored in an external storage device configured to be communicatively coupled to a plurality of memory devices, and wherein the first block of patient data is stored on a first memory device;

retrieving secondary metadata identifying a start time of a second collection time period and a stop time of the second collection period, wherein the second collection period is associated with a second block of patient data pertaining to the first patient, wherein the secondary metadata is stored in the external storage device, and wherein the second block of patient data is stored on a second memory device;

querying the start time and the stop time identified by the metadata and by the secondary metadata for determining a memory device from the plurality of memory devices such that the determined memory device stores patient data pertaining to the first patient, wherein the patient data is associated with the identified collection time period; and retrieving the stored patient data pertaining to the first patient, wherein the stored patient data is associated with the identified collection time period such that the stored patient data is retrieved from the determined memory device in the plurality of memory devices.

2. Data retrieval method of claim 1, wherein the first block of patient data is collected using a first monitor device, wherein the first monitor device is wearable by a patient.

3. Data retrieval method of claim 1, wherein the second block of patient data is collected using a second monitor device.

4. Data retrieval method of claim 1, wherein the external storage device is located at a remote monitoring center.

5. Data retrieval method of claim 1, wherein the metadata further comprises at least one of a device identifier that identifies the monitor device, a data collection time period identifier that identifies the collection time period of interest, and a user identifier that identifies the patient.

6. Data retrieval method according to claim 1, wherein the external storage device is comprised in a communication device.

7. Data retrieval method according to claim 6, wherein the external storage device is located at a remote monitoring center.

8. Telemonitoring method for storing and retrieving blocks of patient data pertaining to the same patient, the method comprising:

collecting, from a first patient, during a first collection time period, a first block of patient data using a first monitor device, wherein the first monitor device is wearable by the first patient, and wherein the first block of patient data pertains to the first patient;

storing, during the first collection period, the first block of patient data on a first memory device configured to be communicatively coupled to the first monitor device;

generating metadata identifying a start time of the first collection period and a stop time of the first collection period;

storing the generated metadata pertaining to the first collection time period on an external storage device configured to be communicatively coupled to the first monitor device;

collecting, from the first patient, during a second collection time period, a second block of patient data using a second monitor device, wherein the second monitor device is wearable by the first patient, and wherein the second block of patient data pertains to the first patient;

storing, during the second collection period, the second block of patient data on a second memory device configured to be communicatively coupled to the second monitor device;

generating secondary metadata identifying a start time of the second collection period and a stop time of the second collection period;

storing the generated secondary metadata pertaining to the second collection time period on the external storage device, wherein the external storage device is further configured to be communicatively coupled to the second monitor device;

receiving a request for a sub-block of patient data associated with a requested collection time period;

retrieving metadata identifying the start time of the first collection time period and the stop time of the first collection time period from the external storage device;

retrieving the secondary metadata identifying the start time of the second collection time period and the stop time of the second collection time period from the external storage device;

querying the start time and the stop time identified by the metadata and by the secondary metadata to determine whether the requested sub-block of patient data associated with the requested collection time period is stored in the first memory device or the second memory device; and retrieving the requested sub-block of patient data associated with the requested collection time period from the first memory device or the second memory device, responsive to the determination whether the requested sub-block of patient data associated with the requested collection time period is stored in the first memory device or the second memory device.

9. Telemonitoring method according to claim 8, wherein the external storage device is located at a remote monitoring center.

10. Telemonitoring system for retrieving blocks of patient data pertaining to the same patient, the system comprising:

a monitoring center configured to communicate with a first data collection device, wherein the first data collection device comprises:

a sensor configured to measure, for a first patient, signals indicating patient data during a first collection time period, a memory device for storing a first block of patient data derived from the signals measured by the sensor, and a communication device for communicating with a monitoring center, wherein the first data collection device is configured to generate metadata, wherein the metadata identifies a start time of the first collection time period and a stop time of the collection time period, wherein the collection time period is associated with the first block of patient data, and wherein the generated metadata is stored in an external storage device configured to be communicatively coupled with the first data collection device;

wherein the monitoring center is further configured to communicate with a second data collection device, wherein the second data collection device comprises:

a sensor configured to measure, for the first patient, signals indicating patient data during a second collection time period, a memory device for storing a second block of patient data derived from the signals measured by the sensor, and a communication device for communicating with a monitoring center, wherein the second data collection device is configured to generate secondary metadata, wherein the secondary metadata identifies a start time of the second collection time period and a stop time of the second collection time period, wherein the second collection time period is associated with the second block of patient data, wherein the generated secondary metadata is stored in the external storage device, and wherein the external storage device is further configured to be communicatively coupled with the second data collection device; wherein the monitoring center is further configured to:

receive a request for a sub-block of patient data associated with a requested collection time period, query the start time and the stop time identified by the metadata and by the secondary metadata stored in the external storage device to determine whether the requested sub-block of patient data associated with the requested collection time period is stored in the memory device of the first data collection device or in the memory device of the second data collection device, and retrieve the requested sub-block of patient data associated with the requested collection time period, responsive to the determination whether the requested sub-block of patient data associated with the requested collection time period is stored in the memory device of the first data collection device or in the memory device of the second data collection device.

11. The telemonitoring system of claim 10, wherein the first data collection device is configured to be worn during the first collection time period by the first patient.

12. The telemonitoring system of claim 10, wherein the external storage device is located at the monitoring center.

13. Telemonitoring system according to claim 10, wherein the system further comprises a phone device, wherein the phone device comprises the external storage device.

* * * * *